US011690575B2

(12) United States Patent
Tanishima et al.

(10) Patent No.: US 11,690,575 B2
(45) Date of Patent: Jul. 4, 2023

(54) APPARATUS AND METHOD FOR PROCESSING PHYSIOLOGICAL INFORMATION

(71) Applicant: NIHON KOHDEN CORPORATION, Tokyo (JP)

(72) Inventors: Masami Tanishima, Tokorozawa (JP); Takashi Mato, Tokyo (JP); Shunichi Miyata, Higashimatsuyama (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 613 days.

(21) Appl. No.: 16/150,659

(22) Filed: Oct. 3, 2018

(65) Prior Publication Data

US 2019/0110759 A1 Apr. 18, 2019

(30) Foreign Application Priority Data

Oct. 12, 2017 (JP) ................................ 2017-198571
Sep. 27, 2018 (JP) ................................ 2018-181521

(51) Int. Cl.
*A61B 5/00* (2006.01)
*A61B 5/0205* (2006.01)
(Continued)

(52) U.S. Cl.
CPC ........ *A61B 5/7282* (2013.01); *A61B 5/02055* (2013.01); *A61B 5/02405* (2013.01);
(Continued)

(58) Field of Classification Search
CPC . A61B 2505/03; A61B 5/02055; A61B 5/021; A61B 5/02405; A61B 5/361;
(Continued)

(56) References Cited

U.S. PATENT DOCUMENTS 6,360,126 B1 * 3/2002 Mika .................... A61N 1/368
607/9
2002/0161291 A1 * 10/2002 Kianl ................. A61B 5/0002
600/324
(Continued)

FOREIGN PATENT DOCUMENTS

JP 2004-248793 A 9/2004
JP 2005-261777 A 9/2005
(Continued)

OTHER PUBLICATIONS

Bill Jelen, Excel Charting Using a Second Axis, Strategic Finance, Nov. 2010, pp. 54-55 (Year: 2010).*
(Continued)

*Primary Examiner* — Jonathan T Kuo
*Assistant Examiner* — Vynn V Huh
(74) *Attorney, Agent, or Firm* — Pearne & Gordon LLP

(57) ABSTRACT

A physiological information processing apparatus includes a processor and a memory storing computer-readable instructions. When the instructions are executed by the processor, the physiological information processing apparatus obtains physiological information data indicative of physiological information of a subject, obtains a first parameter associated with a vital sign of the subject based on the physiological information data, displays a first trend graph showing temporal change in the first parameter in a first display area of a display screen of a display, obtains a second parameter associated with an autonomic nerve function of the subject based on the physiological information data, and displays a second trend graph showing temporal change in the second parameter in a second display area of the display screen. The first and second display areas are displayed next to each other such that time axes of the first and second display areas are synchronized with each other.

13 Claims, 7 Drawing Sheets

(51) Int. Cl.
 *A61B 5/024* (2006.01)
 *A61B 5/363* (2021.01)
 *A61B 5/021* (2006.01)
 *A61B 5/361* (2021.01)
 *G16H 50/30* (2018.01)

(52) U.S. Cl.
 CPC ............ *A61B 5/363* (2021.01); *A61B 5/4035* (2013.01); *A61B 5/7257* (2013.01); *A61B 5/7275* (2013.01); *A61B 5/742* (2013.01); *A61B 5/746* (2013.01); *A61B 5/748* (2013.01); *A61B 5/7435* (2013.01); *A61B 5/7475* (2013.01); *A61B 5/021* (2013.01); *A61B 5/361* (2021.01); *A61B 2505/03* (2013.01)

(58) Field of Classification Search
 CPC ..... A61B 5/363; A61B 5/4035; A61B 5/7257; A61B 5/7275; A61B 5/7282; A61B 5/742; A61B 5/7435; A61B 5/746; A61B 5/7475; A61B 5/748; G16H 50/30
 See application file for complete search history.

(56) References Cited

U.S. PATENT DOCUMENTS

| | | |
|---|---|---|
| 2005/0209522 A1 | 9/2005 | Tadokoro et al. |
| 2006/0161091 A1 | 7/2006 | Kinouchi et al. |
| 2008/0281247 A1 | 11/2008 | Tadokoro et al. |
| 2014/0213919 A1* | 7/2014 | Poon ................ A61B 5/7405 600/509 |
| 2014/0277284 A1* | 9/2014 | Chen ................ A61N 1/37241 607/59 |
| 2015/0160098 A1* | 6/2015 | Noda ................ G05B 23/0281 702/35 |
| 2016/0089040 A1* | 3/2016 | Narusawa ............ A61B 5/1117 600/324 |
| 2016/0228020 A1* | 8/2016 | Matsui ................ A61B 5/361 |
| 2016/0302680 A1* | 10/2016 | Narusawa .......... A61B 5/02405 |

FOREIGN PATENT DOCUMENTS

| | | |
|---|---|---|
| JP | 2016-067480 A | 5/2016 |
| JP | 2016-202348 A | 12/2016 |
| JP | 2017-027123 A | 2/2017 |

OTHER PUBLICATIONS

Yoshimoto et al., "Frequency components of systolic blood pressure variability reflect vasomotor and cardiac sympathetic functions in conscious rats", Jun. 29, 2011, J Physiol Sci, 61:373-383. (Year: 2011).*

Japanese Office Action dated May 10, 2022 issued in Japanese Patent Application No. 2018-181521.

* cited by examiner

APPARATUS AND METHOD FOR PROCESSING PHYSIOLOGICAL INFORMATION

CROSS-REFERENCE TO RELATED APPLICATION

The present application claims priority to Japanese Patent Application No. 2017-198571 filed on Oct. 12, 2017 and Japanese Patent Application No. 2018-181521 filed on Sep. 27, 2018, the entire contents of which are incorporated herein by reference.

BACKGROUND

The presently disclosed subject matter relates to a physiological information processing apparatus, a physiological information processing method, and a computer-readable storage medium storing a program which causes a computer to execute the physiological information processing method.

Related art apparatuses are configured to monitor an autonomic nerve activity of a patient. For example, a related art apparatus is configured to predict or determine an abnormal reaction of a living body based on the autonomic nerve activity of a patient (see, e.g., JP2005-261777A). To visualize the autonomic nerve activity of the patient, frequency analysis is performed on heart rate variability (HRV) of the patient, and a trend graph showing temporal change in the high-frequency component (HF) of the heart rate variability and the ratio (LF/HF) of the low-frequency component (LF) to the high-frequency component is displayed on a display screen of the apparatus.

Medical personnel can more accurately check disease condition of a patient by observing not only temporal change in the autonomic nerve function (e.g., the sympathetic nerve function and the parasympathetic nerve function) of the patient but also temporal change in vital signs of the patient. In order to do so, a medical personnel may consider using two separate apparatuses, i.e., an autonomic nerve activity monitoring apparatus that shows temporal change in the autonomic nerve function and a patient monitoring apparatus that shows temporal change in vital signs. However, this requires the medical personnel to look at two display screens, i.e., a display screen showing temporal change in the autonomic nerve function and another display screen showing temporal change in the vital signs, and it is difficult for the medical personnel to instantaneously understand the disease condition of the patient. From the above viewpoint, there is room to improve usability of the physiological information processing apparatus.

SUMMARY

One or more illustrative aspects of the presently disclosed subject matter provide a physiological information processing apparatus, a physiological information processing method, and a computer-readable storage medium storing a program to cause a computer to execute the physiological information processing method, with improved usability.

According an aspect of the presently disclosed subject matter, a physiological information processing apparatus includes a processor and a memory storing computer-readable instructions. When the computer-readable instructions are executed by the processor, the processor causes the physiological information processing apparatus to obtain at least one set of physiological information data indicative of physiological information of a subject, obtain at least one first parameter associated with a vital sign of the subject based on the physiological information data, display a first trend graph showing temporal change in the first parameter in a first display area of a display screen of a display that displays the physiological information of the subject, obtain at least one second parameter associated with an autonomic nerve function of the subject based on the physiological information data, and display a second trend graph showing temporal change in the second parameter in a second display area of the display screen. The first display area and the second display area are displayed next to each other such that a time axis of the first display area and a time axis of the second display area are synchronized with each other.

According another aspect of the presently disclosed subject matter, a physiological information processing apparatus includes a processor and a memory storing computer-readable instructions. When the computer-readable instructions are executed by the processor, the processor causes the physiological information processing apparatus to obtain at least one set of physiological information data indicative of physiological information of a subject, obtain at least one second parameter associated with an autonomic nerve function of the subject based on the physiological information data, display a second trend graph showing temporal change in the second parameter in a second display area of a display screen of a display that displays the physiological information of the subject, and display event information associated with at least one of the subject and the physiological information processing apparatus in a third display area of the display screen. The second display area and the third display area are displayed next to each other such that a time axis of the second display area and a time axis of the third display area are synchronized with each other.

According another aspect of the presently disclosed subject matter, a physiological information processing method to be executed by a computer is provided. The physiological information processing method includes steps of (a) obtaining at least one set of physiological information data indicative of physiological information of a subject, (b) obtaining at least one first parameter associated with a vital sign of the subject based on the physiological information data, (c) displaying a first trend graph showing temporal change in the first parameter in a first display area of a display screen, (d) obtaining at least one second parameter associated with an autonomic nerve function of the subject based on the physiological information data, and (e) displaying a second trend graph showing temporal change in the second parameter in a second display area of the display screen. The first display area and the second display area are displayed next to each other such that a time axis of the first display area and a time axis of the second display area are synchronized with each other.

According another aspect of the presently disclosed subject matter, a physiological information processing method to be executed by a computer is provided. The physiological information processing method includes steps of (a) obtaining at least one set of physiological information data indicative of physiological information of a subject, (b) obtaining at least one second parameter associated with an autonomic nerve function of the subject based on the physiological information data, (c) displaying a second trend graph showing temporal change in the second parameter in a second display area of a display screen, (d) displaying event information associated with at least one of the subject and the physiological information processing apparatus in a third display area of the display screen. The second display area and the third display area are displayed next to each other such that a time axis of the second display area and a time axis of the third display area are synchronized with each other.

According another aspect of the presently disclosed subject matter, a computer-readable storage medium storing a program which causes a computer to execute the physiological information processing method described above.

DETAILED DESCRIPTION

Hereinafter, embodiments of the presently disclosed subject matter will be described with reference to the drawings.

Figure 1:
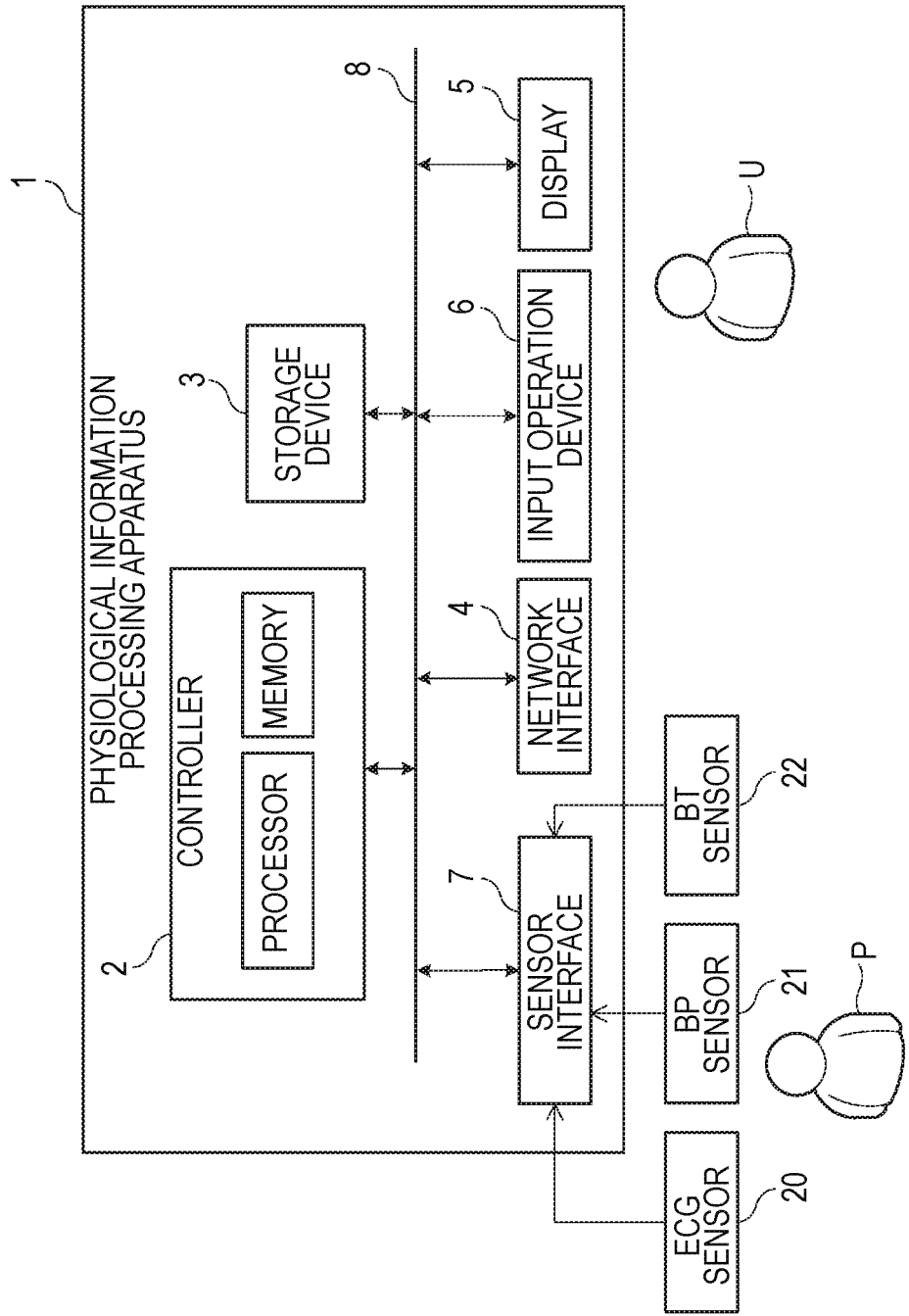
FIG. 1 is a diagram illustrating a hardware configuration of a physiological information processing apparatus according to an embodiment of the presently disclosed subject matter.

FIG. 1 illustrates a hardware configuration of a physiological information processing apparatus 1 according to an embodiment of the presently disclosed subject matter. As illustrated in FIG. 1, the physiological information processing apparatus 1 includes a controller 2, a storage device 3, a network interface 4, a display 5, an input operation device 6 and a sensor interface 7. These are communicably connected to each other through a bus 8.

The processing apparatus 1 may be a patient monitor or the like specifically designed to display a trend graph of a vital sign of a patient P (an example of a subject). Other examples of the processing apparatus 1 include a personal computer, a workstation, a smartphone, a tablet, a wearable device (e.g., a smartwatch or an AR glasses) attachable to a body (e.g., an arm or a head) of a user U (e.g., a medical personnel).

The controller 2 includes at least one memory and at least one processor. The at least one memory is configured to store computer-readable instructions (programs). For example, the at least one memory may include a read only memory (ROM) storing various programs, a RAM random access memory (RAM) having a plurality of work areas storing various programs to be executed by a processor, and/or a flash memory. The at least one processor may include a central processing unit (CPU), a micro processing unit (MPU) and/or a graphics processing unit (GPU). The CPU may include a plurality of CPU cores. The GPU may include a plurality of GPU cores. The at least one processor may be configured to load a designated program stored in the storage device 3 or in the ROM to the RAM, and to execute various processings in cooperation with the RAM.

In particular, the controller 2 may control various operations of the processing apparatus 1 by the processor loading a physiological information processing program to the RAM and executing the program in cooperation with the RAM. Details of the physiological information processing program will be described later.

The storage device 3 may include, for example, a hard disk drive HDD), a solid state drive (SSD), and/or a flash memory, and is configured to store programs and various sets of data. The physiological information processing program may be stored in the storage device 3. Physiological information data (electrocardiogram data, blood pressure data, body temperature data, etc.) indicative of physiological information of a patient P may be saved in the storage device 3. For example, the electrocardiogram data obtained by an electrocardiogram sensor 20 may be saved in the storage device 3 through the sensor interface 7.

The network interface 4 is configured to connect the processing apparatus 1 to a communication network. Specifically, the network interface 4 may include various wired connection terminals to communicate with an external apparatus such as a server through the communication network. The network interface 4 may include various processing circuits, an antenna and the like to wirelessly communicate with an external apparatus. The standard for the wireless communication between the external apparatus and the processing apparatus 1 may be Wi-Fi (trademark), Bluetooth (trademark), ZigBee (trademark) or LPWA. The communication network may be a local area network (LAN), a wide area network (WAN), the Internet or the like. For example, the physiological information processing program and the physiological information data may be obtained through the network interface 4 from a server on the communication network.

Figure 4:
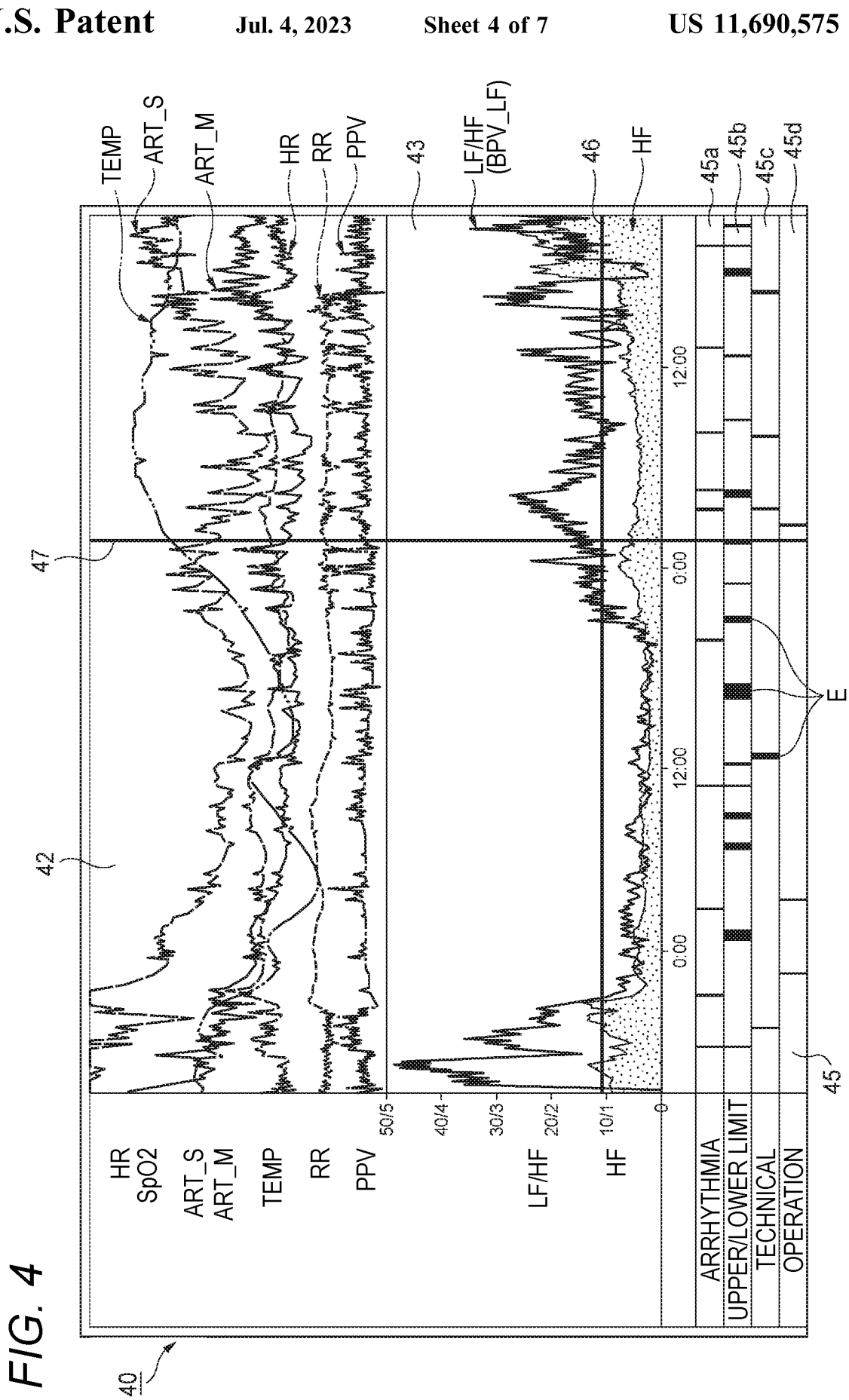
FIG. 4 is a view illustrating an example of a display screen displayed on a display.

The display 5 may be a liquid crystal display or an organic EL display, or may be a transmissive or a nontransmissive head mounted display attachable to a user's head. Alternatively, the display 5 may be a projector that projects an image onto a screen. For example, a display screen 40 illustrated in FIG. 4 is displayed on the display 5. The display screen 40 is a user interface screen such as a GUI screen. The processing apparatus 1 may not have the display 5. For example, the display screen 40 may be displayed on a display of an external apparatus such as a central monitor communicably connected to the processing apparatus 1. In this case, the processing apparatus 1 may display, on the display of the external apparatus, the display screen 40 displaying a trend graph associated with a vital sign and a trend graph associated with an autonomic nerve function through the network interface 4 or an input interface (not shown).

The input operation device 6 is configured to accept an input operation by a user U (e.g., a medical personnel) operating the processing apparatus 1 and to generate an instruction signal corresponding to the input operation. The input operation device 6 may be, for example, a touch panel superposed on the display 5, an operation button provided on a housing, a mouse and/or a keyboard. The instruction signal generated by the input operation device 6 is sent to the controller 2 through the bus 8, and the controller 2 executes a predetermined operation in response to the instruction signal.

The sensor interface 7 is configured to connect vital sensors such as the electrocardiogram sensor 20, a blood pressure sensor 21 and a body temperature sensor 22 to the processing apparatus 1. The sensor interface 7 may include an input terminal configured to receive physiological information data output from the sensors. The sensor interface 7 may include various processing circuits, an antenna and the like to wirelessly communicate with the sensors. The electrocardiogram sensor 20 is configured to obtain electrocardiogram data of a patient P. The electrocardiogram data is indicative of electrocardiographic waveform of the patient P. The blood pressure sensor 21 is configured to obtain blood pressure data of the patient P. The blood pressure data is indicative of temporal change in the blood pressure of the patient P. The body temperature sensor 22 is configured to obtain the body temperature data of the patient P. The body temperature data is indicative of temporal change in the body temperature of the patient P. The electrocardiogram data, the blood pressure data and the body temperature data are examples of physiological information data indicative of physiological information of the patient P. In the illustrated example, the electrocardiogram data, the blood pressure data and the body temperature data are obtained as examples of the physiological information data. Other examples of the physiological information data that may be further obtained include SpO2 data indicative of temporal change in SpO2 (arterial blood oxygen saturation), CO2 data indicative of temporal change in CO2 value (e.g., CO2 concentration or CO2 discharge amount), respiration data indicative of temporal change in a respiratory rate (RR) of the patient, and intracranial data indicative of temporal change in an intracranial pressure (ICP).

Figure 2:
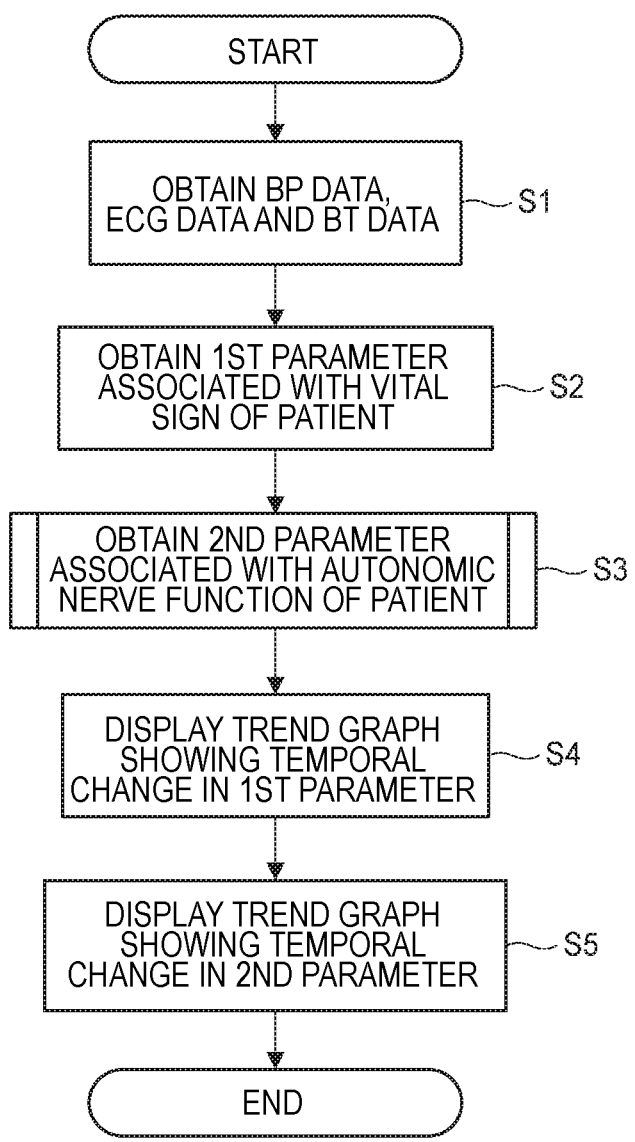
FIG. 2 is a flowchart illustrating a physiological information processing method according to an embodiment of the presently disclosed subject matter.
Figure 3:
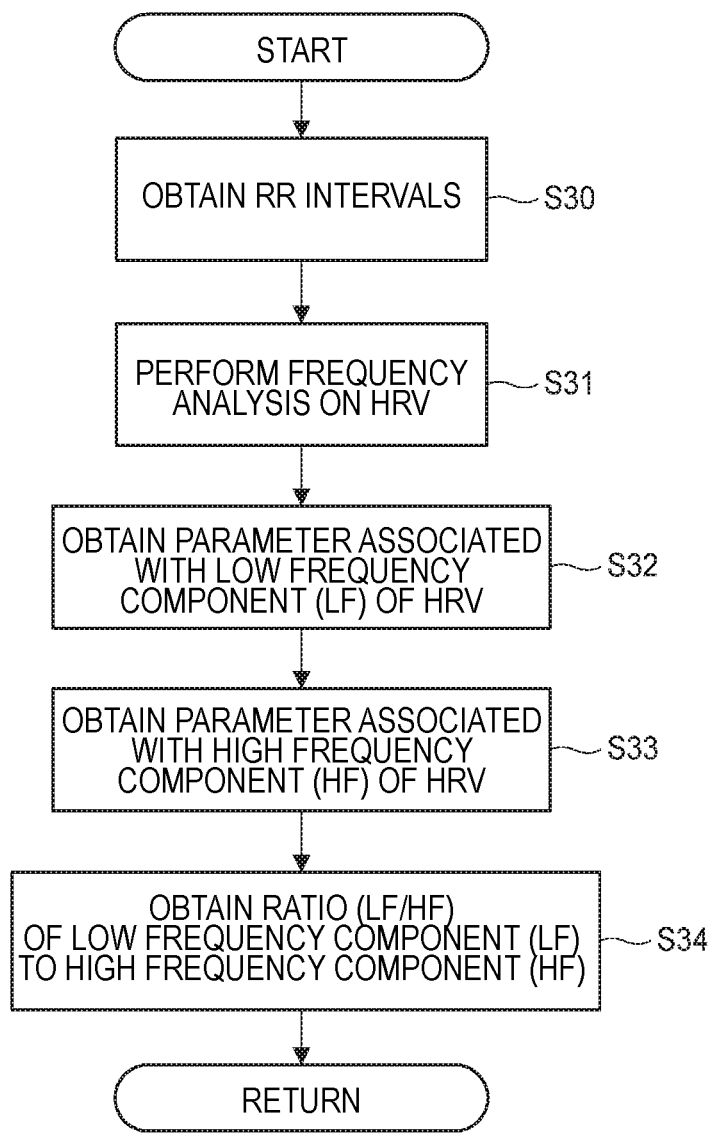
FIG. 3 is a flowchart illustrating an example of the processing of obtaining a parameter associated with the autonomic nerve function of a patient.

Next, the physiological information processing method according to the present embodiment will be described by referring to FIGS. 2 to 4. FIG. 2 is a flowchart illustrating the physiological information processing method according to the present embodiment. FIG. 3 is a flowchart illustrating an example of the processing of obtaining a parameter associated with the autonomic nerve function of the patient P. FIG. 4 is a view illustrating an example of the display screen 40 (GUI screen) displayed on the display 5.

As illustrated in FIG. 2, at step S1, the controller 2 obtains the blood pressure data, the electrocardiogram data and the body temperature data as physiological information data. Specifically, when the physiological information data is obtained in real time, the controller 2 may obtain the electrocardiogram data from the electrocardiogram sensor 20 in real time, obtain the blood pressure data from the blood pressure sensor 21 in real time and obtain the body temperature data from the body temperature sensor 22 in real time. On the other hand, the controller 2 may obtain the physiological information data such as the blood pressure data, the electrocardiogram data and the body temperature data stored in the storage device 3. Further, the controller 2 may obtain the physiological information data through a server or the like disposed on the communication network. It may be only the electrocardiogram data that the controller 2 obtains. Moreover, the controller 2 may obtain at least one of the SpO2 data, the CO2 data, the respiration data and the intracranial data as the physiological information data.

Then, at step S2, the controller 2 obtains a parameter (an example of the first parameter) associated with a vital sign of the patient P based on the physiological information data (e.g., the electrocardiogram data, the blood pressure data, the body temperature data). In particular, the controller 2 may obtain data indicative of temporal change in the parameter associated with a vital sign of the patient P based on the physiological information data. As illustrated in FIG. 4, the parameter associated with the vital sign is, for example, the heart rate (HR), the blood oxygen saturation (SpO2), the body temperature (TEMP), the pulse pressure variability (PPV), the average blood pressure value (ART_M), the maximum blood pressure value (ART_S) and/or the respiratory rate (RR). As the parameter associated with the vital sign, the CO2 value or the intracranial pressure (ICP) may be obtained. When the physiological information data is obtained in real time, the controller 2 may execute the step S2 after obtaining the physiological information data during a predetermined period.

Then, at step S3, the controller 2 obtains a parameter (an example of the second parameter) associated with the autonomic nerve function of the patient P based on the physiological information data (e.g., the electrocardiogram data, the blood pressure data). In particular, the controller 2 may obtain data indicative of temporal change in the parameter associated with the autonomic nerve function of the patient P based on the physiological information data. Referring to FIG. 3, the processing of obtaining the parameter associated with the autonomic nerve function of the patient P will be described below.

As illustrated in FIG. 3, at step S30, the controller 2 obtains a plurality of RR intervals based on the electrocardiogram data. Here, the RR interval is the interval between the R wave of a heartbeat waveform (QSR waveform) and the R wave of the adjacent heartbeat waveform. For example, the controller 2 may identify the plurality of RR intervals by identifying the times of the peak points of a plurality of R waves from the electrocardiogram data. Then, the controller 2 performs frequency analysis on the heat rate variability (HRV) of the patient P (step S31). Specifically, the controller 2 performs frequency analysis (e.g., the wavelet analysis or the fast Fourier transformation (FFT)) on the RR interval data indicative of temporal fluctuation in the RR interval. Here, the RR interval data may include a plurality of RR intervals of each time. Moreover, the RR interval data may include a plurality of heart rates n (n is a natural number) and a plurality of RR intervals Rn each associated with one of the plurality of heart rates n. For example, the n-th RR interval Rn is defined by the interval between the R wave of the n-th heartbeat waveform Wn and the R wave of the (n+1)-th heartbeat waveform Wn+1.

Then, the controller 2 obtains a parameter associated with the low frequency component (LF) of the heart rate variability (HRV) (step S32). For example, the controller 2 may identify the peak intensity of the power spectrum of the RR interval data in a low frequency band (e.g., 0.05 Hz to 0.15 Hz) or the integral value of the intensity as the parameter associated with the low frequency component (LF) of the heat rate variability (hereinafter, LF parameter). The controller 2 may obtain the LF parameter at a time t1 (or a time t2) by performing frequency analysis on the RR interval data between the times t1 and t2 (t1<t2).

Then, the controller 2 obtains a parameter associated with the high frequency component (HF) of the heart rate variability (HRV) (step S33). For example, the controller 2 may identify the peak intensity of the power spectrum of the RR interval data in a high frequency band (e.g., 0.15 Hz to 0.40 Hz) or the integral value of the intensity as the parameter associated with the high frequency component (HF) of the heat rate variability (hereinafter, HF parameter). The controller 2 may obtain the HF parameter at the time t2 (or a time t3) by performing frequency analysis on the RR interval data between the times t2 to t3 (t2<t3). The HF parameter is a parameter associated with the parasympathetic nerve function of the patient P. For example, the medical personnel can determine that the parasympathetic nerve function of the patient P has deteriorated when the value of the HF parameter is lower than a predetermined threshold value during a predetermined period.

Then, the controller 2 obtains the ratio (LF/HF) of the low frequency component (LF) of the heart rate variability to the high frequency component (HF) of the heat rate variability (step S34). Specifically, the controller 2 obtains the ratio of the LF parameter to the HF parameter as an LF/HF parameter. The LF/HF parameter is a parameter associated with the sympathetic nerve function of the patient P. For example, the medical personnel can determine that the sympathetic nerve function of the patient P has deteriorated when the value of the LF/HF parameter is lower than a predetermined threshold value during a predetermined period.

As described above, the controller 2 can obtain the parameters associated with the autonomic nerve function of the patient P from the electrocardiogram data. In particular, the controller 2 can obtain the HF parameter indicative of the parasympathetic nerve function of the patient P and the LF/HF parameter indicative of the sympathetic nerve function of the patient P from the electrocardiogram data.

The controller 2 may obtain a parameter associated with the autonomic nerve function of the patient P from the blood pressure data. In this case, the controller 2 performs frequency analysis on the maximum blood pressure variability (BPV) of the patient P after obtaining the blood pressure data. Specifically, the controller 2 performs frequency analysis (e.g., the wavelet analysis or the fast Fourier transformation (FFT)) on the maximum blood pressure data after obtaining the maximum blood pressure data indicative of temporal change in the maximum blood pressure of the patient P. Thereafter, the controller 2 obtains a parameter associated with the low frequency component (LF) of the maximum blood pressure variability (BPV). For example, the controller 2 identifies the peak intensity of the power spectrum of the maximum blood pressure data in the low frequency band or the integral value of the intensity as the parameter associated with the low frequency component (LF) of the BPV (hereinafter, BPV_LF parameter). The BPV_LF parameter is a parameter associated with the sympathetic nerve function of the patient P. For example, the medical personnel can determine that the sympathetic nerve function of the patient P has deteriorated when the value of the BPV_LF parameter is lower than a predetermined threshold value during a predetermined period.

Returning to FIG. 2, at step S4, the controller 2 displays, in a display area 42 (first display area) of the display screen 40, a trend graph (an example of the first trend graph) showing temporal change in a parameter (e.g., the heart rate (HR)) associated with a vital sign of the patient P (see FIG. 4). As illustrated in FIG. 4, trend graphs of the heart rate, the body temperature, the pulse pressure variability, the average blood pressure value, the maximum blood pressure value and the respiratory rate (RR) may be displayed in the display area 42.

Then, at step S5, the controller 2 displays, in a display area 43 (second display area) of the display screen 40, a trend graph (an example of the second trend graph) showing temporal change in a parameter associated with the autonomic nerve function of the patient P. As illustrated in FIG. 4, the controller 2 may display, in the display area 43, a trend graph of the HF parameter associated with the parasympathetic nerve function of the patient P and a trend graph of the LF/HF parameter associated with the sympathetic nerve function of the patient P.

A trend graph of the BPV_LF parameter may be displayed in the display area 43 as the LF/HF parameter as the trend graph of the parameter associated with the sympathetic nerve function. In this case, display switching between the trend graph of the LF/HF parameter and the trend graph of the BPV_LF parameter may be made in accordance with an input operation by the user U. When the display switching from the trend graph of the LF/HF parameter to the trend graph of the BPV_LF parameter is made, the value of the scale and the threshold value may be changed according to the trend graph of the BPV_LF parameter.

As illustrated in FIG. 4, the display area 42 and the display area 43 are displayed next to each other such that the time axis of the display area 42 and the time axis of the display area 43 are synchronized with each other. In other words, the time axis of the trend graph of the vital sign displayed in the display area 42 and the time axis of the trend graph of the autonomic nerve function displayed in the display area 43 coincide with each other (that is, these two trend graphs share one time axis). As described above, the user U (medical personnel) can more accurately and quickly check the disease condition of the patient by visually confirming the temporal change in the vital sign and the autonomic nerve function of the patient P displayed on the display screen 40. In particular, the user U can see changes of the disease condition of the patient P, the risk of occurrence of arrhythmia and the like. As described above, the processing apparatus 1 with improved usability can be provided.

When the physiological information data (e.g., the electrocardiogram data, the blood pressure data, the body temperature data) is obtained from the sensors in real time, at steps S4 and S5, the controller 2 may update the trend graph (an example of the first trend graph) of the vital sign and the trend graph (an example of the second trend graph) of the autonomic nerve function according to the lapse of time. In this case, the series of processing illustrated in FIG. 2 may be repetitively executed at predetermined intervals. The value of the trend graph shown at the right end of the display screen 40 is the newest value, whereas the value of the trend graph shown at the left end of the display screen 40 is the oldest value.

As described above, when the trend graph of the vital sign and the trend graph of the autonomic nerve function are updated according to the lapse of time, the medical personnel can check the condition of the patient in real time by visually confirming these trend graphs updated in real time on the display screen 40. As described above, the usability of the processing apparatus 1 can be further improved.

As illustrated in FIG. 4, a threshold indicator bar 46 indicating a threshold value Vth1 of the LF/HF parameter associated with the sympathetic nerve function and a threshold value Vth2 of the HF parameter associated with the parasympathetic nerve function are displayed in the display area 43. The threshold indicator bar 46 is used to determine abnormality of the sympathetic nerve function of the patient P and/or abnormality of the parasympathetic nerve function. For example, it is assumed that the threshold value Vth1 of the LF/HF parameter is 10 (msec/Hz1/2) and the threshold value Vth2 of the HF parameter is 1 (msec/Hz1/2). In this case, when the scale interval K1 of the longitudinal axis of the display area 43 with respect to the LF/HF parameter is 10 (msec/Hz1/2) and the scale interval K2 of the longitudinal axis of the display area 43 with respect to the HF parameter is 1 (msec/Hz1/2), a single threshold indicator bar 46 can be displayed in the display area 43. That is, when the following relational expression (1) holds, a single threshold indicator bar 46 can be displayed in the display area 43:

$$Vth1/Vth2 = K1/K2 \qquad (1)$$

According to the present embodiment, since the threshold indicator bar 46 is displayed in the display area 43, the user U can instantaneously confirm whether there is abnormality in the autonomic nerve function of the patient P by visually confirming the trend graph of the autonomic nerve function and the threshold indicator bar 46. For example, the user U can intuitively see whether there is abnormality in the sympathetic nerve function and/or abnormality in the parasympathetic nerve function of the patient P by visually confirming the single threshold indicator bar 46 indicating the threshold values of the two parameters. Clinically, the medical personnel may determine that the brain stem function of the patient P has deteriorated when the value of the trend graph of the LH/HF parameter and the value of the trend graph of the HF parameter are lower than the threshold indicator bar 46. Moreover, the medical personnel can intuitively understand a sign of the occurrence of arrhythmia (AF, VT) and the condition of the patient P in a catamnestic observation and the like having an influence on the autonomic nerve such as sepsis, hypothermia and tetanus. As described above, the usability of the processing apparatus 1 can be improved.

The threshold indicator bar 46 may be movable in accordance with an input operation from the user U. For example, the threshold indicator bar 46 may be moved by dragging and dropping the threshold indicator bar 46 by use of a mouse. When the input operation device 6 includes a touch panel that accepts an input operation from the user U, the threshold indicator bar 46 may be moved by a touch operation by a finger of the user U.

As described above, when the threshold indicator bar 46 is movable, it is possible to set a threshold indicator bar 46 to determine abnormality of the autonomic nerve function (that is, a threshold value of a parameter associated with the autonomic nerve function) for each patient or for each health care facility. Consequently, the usability of the processing apparatus 1 can be further improved.

It is preferable that the threshold value Vth1 of the LF/HF parameter be changed, for example, within a range of 5 to 10 (msec/Hz1/2). Further, it is preferable that the threshold value Vth2 of the HF parameter be changed, for example, within a range of 0.5 to 1 (msec/Hz1/2). Moreover, when the BPV_LF parameter is used instead of the LF/HF parameter, it is preferable that the threshold value of the BPV_LF parameter be changed within a range of 0.5 to 1 (msec/Hz1/2).

While the single threshold indicator bar 46 indicating threshold values of the two parameters is displayed in the display area 43 in the present embodiment, two threshold indicator bars of a threshold indicator bar indicating the threshold value Vth1 of the LF/HF parameter and a threshold indicator bar indicating the threshold value Vth2 of the HF parameter may be displayed in the display area 43.

As illustrated in FIG. 4, a time indicator bar 47 may be displayed on the display screen 40. The time indicator bar 47 is movable in accordance with an input operation from the user U. As described above, by using the time indicator bar 47, changes of the disease condition of the patient P can be observed more accurately. For example, by moving the time indicator bar 47 to a given position, the user U can confirm the measurement value corresponding to the after-movement position and can display part of the trend graph corresponding to the after-movement position so as to be enlarged. As described above, the user U can intuitively understand the condition of the patient P.

Figure 5:
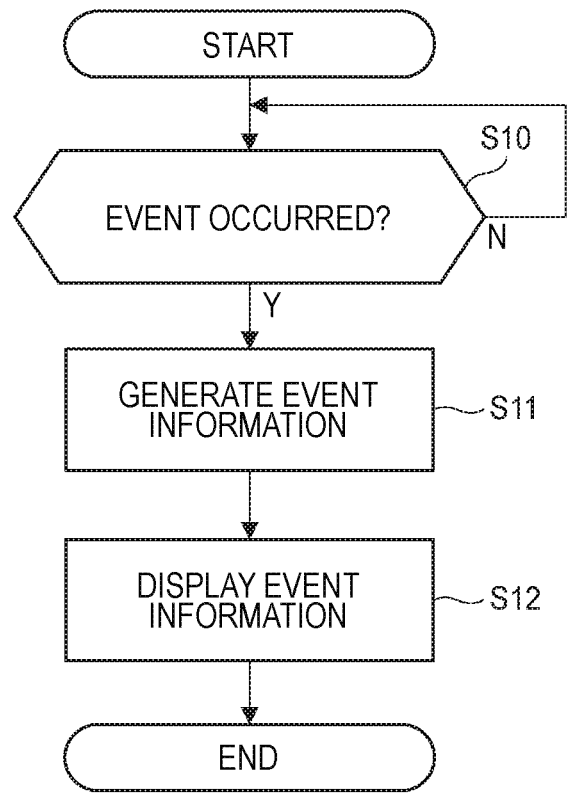
FIG. 5 is a flowchart illustrating an example of the processing of displaying event information.

Next, an example of the processing of displaying event information will be described below by referring to FIG. 4 and FIG. 5. FIG. 5 is a flowchart illustrating the example of the processing of displaying event information. As illustrated in FIG. 5, at step S10, the controller 2 determines whether an event associated with the patient P and/or the processing apparatus 1 has occurred.

When the determination result at step S10 is YES, the controller 2 executes the step S11. When the determination result of step S10 is NO, the controller 2 waits until an event occurs. Then, the controller 2 generates event information associated with the patient P and/or the processing apparatus 1 (step S11). Then, the controller 2 displays the event information in a display area 45 (third display area) of the display screen 40 (step S12).

As illustrated in FIG. 4, the display area 45, the display area 43 and the display area 42 are displayed next to each other such that the time axis of the display area 45, the time axis of the display area 43 and the time axis of the display area 42 are synchronized with each other. In other words, the time axis of the display area 42, the time axis of the display area 43 and the time axis of the display area 45 coincide with one another, and the display areas 42, 43 and 45 share a single time axis. Moreover, the display area 45 has a plurality of segments 45a to 45d.

The event information includes event information associated with the patient P and/or event information associated with the processing apparatus 1. The event information associated with the patient P may include at least one of event information indicating the occurrence of arrhythmia, event information indicating abnormality of the parameter (an example of the first parameter) associated with a vital sign of the patient P, and event information associated with a treatment on the patient P. The event information associated with the processing apparatus 1 may include event information associated with abnormality of the processing apparatus 1 or a failure of attachment between the processing apparatus 1 and an external sensor such as the electrocardiogram sensor 20.

Referring to FIG. 5, the processing of displaying event information indicating the occurrence of arrhythmia will be described below. As illustrated in FIG. 5, at step S10, the controller 2 determines whether arrhythmia has occurred based on the electrocardiogram data. For example, the controller 2 may automatically determine whether arrhythmia has occurred at least based on the RR interval variability (HRV).

When the determination result at step S10 is YES, after generating event information indicating the occurrence of arrhythmia (step S11), the controller 2 displays the event information in the segment 45a of the display area 45 (step S12). For example, when arrhythmia occurs during a period from times t4 to t5, an event indicator bar E may be displayed as the event information in a part of the segment 45a corresponding to the period from the time t4 to the time t5.

The breadth of the event indicator bar E may be adjusted according to the period during which arrhythmia is occurring. For example, the breadth of the event indicator bar E may be increased as the period during which arrhythmia is occurring is increased. Moreover, although not shown, the color of the event indicator bar E may be changed according to the severity of the event. For example, the color of the event indicator bar E is displayed in three colors (red, yellow, blue). In this case, when the level of the event (the occurrence of arrhythmia) indicates an emergency level, the event indicator bar E may be displayed in red. Moreover, when the level of the event indicates an alert level, the event indicator bar E may be displayed in yellow. Further, when the level of the event indicates a caution level, the event indicator bar E may be displayed in blue.

Next, the processing of displaying event information indicating abnormality of the parameter (an example of the first parameter) associated with vital signs will be described below. As illustrated in FIG. 5, at step S10, the controller 2 obtains a plurality of parameters (the heart rate, etc.) associated with vital signs of the patient P based on the physiological information data (e.g., the electrocardiogram data, the blood pressure data, the body temperature data).

The controller 2 determines whether at least one of a plurality of parameters associated with the vital signs is outside a normal range. When the determination result at step S10 is YES, after generating event information indicating the abnormality of the parameter associated with the vital sign (step S11), the controller 2 displays the event information in the segment 45b of the display area 45 (step S12). For example, when the abnormality of the parameter associated with the vital sign occurs during a period from times t6 to t7, the event indicator bar E may be displayed as the event information in a part of the segment 45b corresponding to the period from the time t6 to the time t7.

Next, the processing of displaying event information associated with the processing apparatus 1 will be described below. As illustrated in FIG. 5, at step S10, the controller 2 determines whether abnormality has occurred in the processing apparatus 1 or whether an attachment failure has occurred between the processing apparatus 1 and an external sensor (the electrocardiogram sensor 20, etc.).

When the determination result at step S10 is YES, after generating event information associated with the processing apparatus 1 (step S11), the controller 2 displays the event information in the segment 45c of the display area 45 (step S12). For example, when the abnormality of the processing apparatus 1 or the attachment failure between the processing apparatus 1 and an external sensor occurs during a period from times t8 to t9, the event indicator bar E may be displayed as the event information in a part of the segment 45c corresponding to the period from the time t8 to the time t9.

Next, the processing of displaying event information associated with a treatment on the patient P will be described below. As illustrated in FIG. 5, at step S10, the controller 2 determines whether a predetermined input operation from the user U (e.g., a medical personnel) has been accepted. For example, the user U performs a predetermined input operation to the processing apparatus 1 when a predetermined treatment (medication, etc.) is performed on the patient P.

When the determination result at step S10 is YES, after generating event information associated with the treatment on the patient P (step S11), the controller 2 displays the event information in the segment 45d of the display area 45 (step S12). For example, when the user U performs the treatment on the patient P during a period from times t10 to t11, the event indicator bar E may be displayed as the event information in a part of the segment 45d corresponding to the period from the times t10 to t11.

According to the present embodiment, medical personnel can accurately and quickly check the disease condition of the patient P by visually confirming temporal change in vital signs of the patient, temporal change in the autonomic nerve function of the patient P and event information (event information indicating the occurrence of arrhythmia, etc.) displayed on the display screen 40 (GUI screen). As described above, the usability of the processing apparatus 1 can be further improved.

Figure 6:
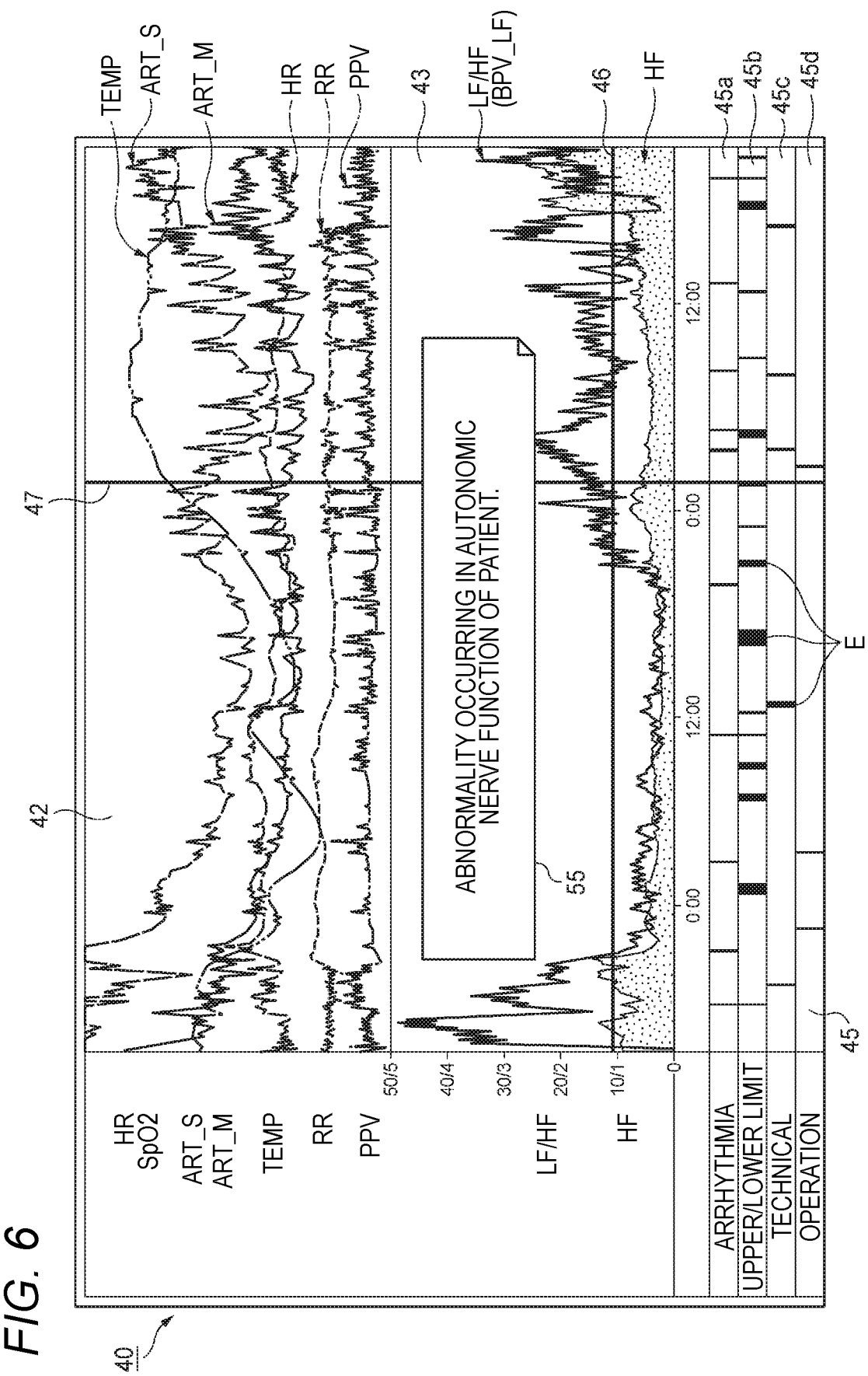
FIG. 6 is a view illustrating a condition where a pop-up notification is displayed on the display screen as an example of presentation of an alert to a medical personnel.

As illustrated in FIG. 6, an alert may be presented to the user U (medical personnel) by displaying a pop-up notification 55 on the display screen 40. Specifically, the controller 2 may display the pop-up notification 55 on the display screen 40 when determining that at least one of the parameter (an example of the first parameter) associated with a vital sign of the patient P and the parameter (an example of the second parameter) associated with the autonomic nerve function of the patient P indicates abnormality.

For example, when determining that the parameter associated with the autonomic nerve function of the patient P is lower than a predetermined threshold value during a predetermined period, the controller 2 may display, on the display screen 40, the pop-up notification 55 indicating that abnormality is occurring in the autonomic nerve function of the patient P. More specifically, the controller 2 may display the pop-up notification 55 on the display screen 40 when it determines that the LH/HF parameter is lower than the threshold value Vth1, that the HF parameter is lower than the threshold Vth2 and that the LF parameter, not shown, is lower than the threshold value Vth3 for a predetermined period.

When the HF parameter shows abnormality, the controller 2 may present an alert (specifically, an alert associated with abnormality in the intracranial pressure) to the user U. In this regard, it has been experimentally shown that the HF parameter increases in accordance with an increase in the intracranial pressure (ICP). Thus, the increase in the intracranial pressure (in other words, the abnormality in the intracranial pressure) can be determined non-invasively based on the increase in the HF parameter. Specifically, the controller 2 may display, on the display screen 40, a pop-up notification indicating a possible increase in the intracranial pressure of the patient when it determines that the HF parameter has exceeded the threshold value Vth2 as a result of continuous increase in the HF parameter (Condition 1). The controller 2 may display, on the display screen 40, a pop-up notification indicating a possible increase in the intracranial pressure of the patient when it determines that the HF parameter has rapidly exceeded the threshold value Vth2 within a short period of time (Condition 2). The controller 2 may also display, on the display screen 40, a pop-up notification indicating a possible abnormality in the brainstem due to the increase in the intracranial pressure of the patient when it determines that the HF parameter and the LH/HF parameter has largely dropped in a short period of time under a condition in which Condition 1 or Condition 2 is met.

As described above, since an alert (e.g., a pop-up notification) is presented to the user U when at least one of the parameter associated with a vital sign and the parameter associated with the autonomic nerve function indicates abnormality, the user U can immediately become aware of the abnormality of the vital sign and/or the autonomic nerve function of the patient P. In particular, since the alert indicating the abnormality in the intracranial pressure is presented to the user U when the HF parameter shows abnormality, the user U can non-invasively recognize the abnormality in the intracranial pressure of the patient P. Other than a visible alert such as the pop-up notification described above or a message, the processing apparatus 1 may present an alert to the user U in an audible, haptic, or olfactory manner.

Figure 7:
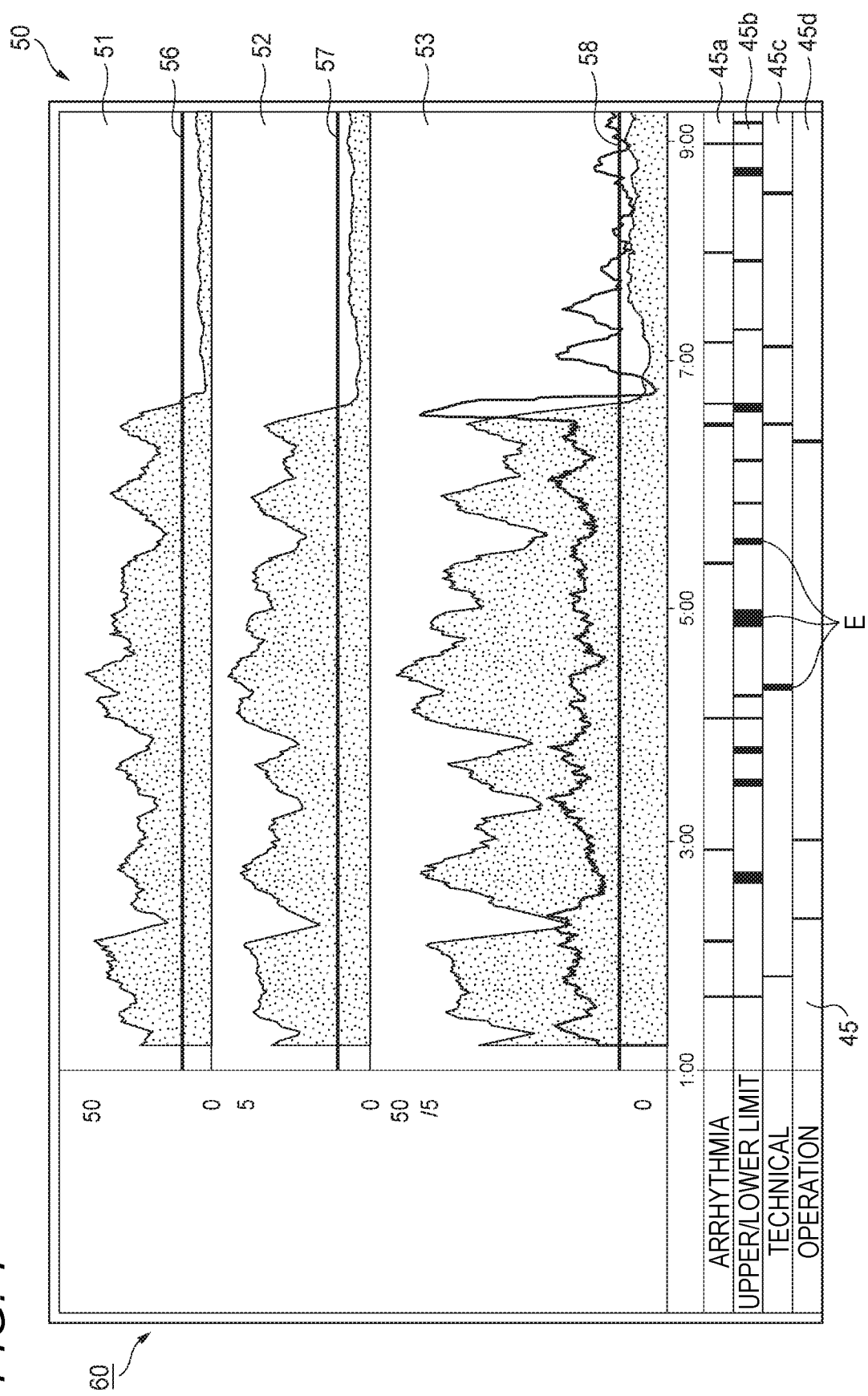
FIG. 7 is a view illustrating another example of the display screen displayed on the display.

Next, referring to FIG. 7, another example of the display screen displayed on the display 5 will be described below. FIG. 7 is a view illustrating another example of a display screen 60 (GUI screen) displayed on the display 5. As illustrated in FIG. 7, the display screen 60 has a display area 50 where trend graphs of the parameters associated with the autonomic nerve function of the patient P are displayed and the display area 45 where event information is displayed.

The display area 50 has a display area 51 where the trend graph of the LF parameter is displayed, a display area 52 where the trend graph of the HF parameter is displayed, and a display area 53 where the trend graph of the HF parameter and the trend graph of the LF/HF parameter are displayed.

A threshold indicator bar 56 indicating the threshold value Vth3 of the LF parameter is displayed in the display area 51, and a threshold indicator bar 57 indicating the threshold value Vth2 of the HF parameter is displayed in the display area 52. A threshold indicator bar 58 indicating the threshold value of the HF parameter and the threshold value Vth1 of the LF/HF parameter are displayed in the display area 53. The display area 50 where the trend graph of the autonomic nerve function is displayed (an example of a second display area) and the display area 45 where the event information is displayed (an example of a third display area) are displayed next to each other such that the time axis of the display area 50 and the time axis of the display area 45 are synchronized with each other. As described above, since the user U (e.g., a medical personnel) can more accurately and quickly check the disease condition of the patient by visually confirming temporal change in the autonomic nerve function of the patient and the event information displayed on the display screen 60, the usability of the processing apparatus 1 can be improved.

To implement the processing apparatus 1 by means of software, a physiological information processing program may be pre-installed in the storage device 3 or a ROM. Alternatively, the physiological information processing program may be stored in a computer-readable storage medium such as a magnetic disk (e.g., an HDD, a floppy disk), an optical disk (e.g., a CD-ROM, a DVD-ROM, Blu-ray (trademark) disc), a magneto-optical disk (e.g., an MO) or a flash memory (e.g., an SD card, a USB memory, or an SSD). In this case, the physiological information processing program stored in the storage medium may be installed in the storage device 3. The processor may load the physiological information processing program stored in the storage device 3 to the RAM and execute the program loaded to the RAM. This is how the physiological information processing method may be executed by the processing apparatus 1.

The physiological information processing program may be downloaded through the network interface 4 from a computer on the communication network. In this case, the downloaded program may be similarly installed in the storage device 3.

While the presently disclosed subject matter has been described with reference to certain embodiments thereof, the scope of the presently disclosed subject matter n is not limited to the embodiments described above, and it will be understood by those skilled in the art that various changes and modifications may be made therein without departing from the scope as defined by the appended claims.

What is claimed is:

1. A physiological information processing apparatus comprising:
   a processor; and
   a memory storing computer-readable instructions, wherein, when the computer-readable instructions are executed by the processor, the processor causes the physiological information processing apparatus to:
      obtain a set of physiological information data indicative of physiological information of a subject, the physiological information data including blood pressure data,
      obtain a first parameter associated with a vital sign of the subject based on the physiological information data,
      display a first trend graph showing a temporal change in the first parameter in a first display area of a display screen of a display that displays the physiological information of the subject,
      obtain at least one second parameter associated with an autonomic nerve function of the subject based on the blood pressure data, the at least one second parameter being a parameter associated with a low frequency component of a maximum blood pressure variability,
      display a second trend graph showing a temporal change in the at least one second parameter with a threshold indicator bar indicating a threshold value in a second display area of the display screen, wherein the threshold indicator bar is movable higher or lower according to a user input, and the processor is configured to display a notification when the at least second parameter is lower than the threshold value, and
      display event information associated with the subject and event information associated with the physiological information processing apparatus in a third display area of the display screen,
   wherein the first display area, the second display area, and the third display area are displayed next to one another such that the first trend graph over a first time axis of the first display area or the second trend graph over a second time axis of the second display area, is synchronized with the event information associated with the physiological information processing apparatus over a third time axis of the third display area,
   wherein the event information associated with the subject includes:
      first event information indicative of an occurrence of arrhythmia with a first bar having a width representing a time period during which the arrhythmia occurs in synchronization with the first graph relating to the vital sign and the second trend graph relating to the autonomic nerve function;
      second event information indicative of an abnormality of the first parameter with a second bar having a width representing a time period during which the abnormality of the first parameter occurs in synchronization with the first and second graphs; and
      third event information associated with a medical treatment on the subject with a third bar having a width representing a time period during which the medical treatment performed to the subject occurs in synchronization with the first and second graphs, and
   wherein the event information associated with the physiological information processing apparatus indicates an abnormality of the physiological information processing apparatus or a failure of attachment between the physiological information processing apparatus and an external sensor configured to obtain the physiological information data, wherein the event information with the physiological information processing apparatus includes a fourth bar having a width representing a time period during which the abnormality of the physiological information processing apparatus or the failure of attachment between the physiological information processing apparatus and the external sensor.

2. The physiological information processing apparatus according to claim 1, wherein the physiological information processing apparatus is configured to display the second trend graph and a threshold indicator bar indicative of a threshold value of the at least one second parameter in the second display area.

3. The physiological information processing apparatus according to claim 2, wherein the threshold indicator bar is movable in accordance with an input operation from a user.

4. The physiological information processing apparatus according to claim 2, wherein the at least one second parameter includes a plurality of second parameters, the plurality of second parameters comprising:
   a first parameter associated with a sympathetic nerve function of the subject; and
   a second parameter associated with a parasympathetic nerve function of the subject,
   wherein the physiological information processing apparatus displays, in the second display area, the second trend graph showing the temporal change in the first parameter associated with the sympathetic nerve function and showing the temporal change in the second parameter associated with the parasympathetic nerve function, and
   wherein the threshold indicator bar is a single threshold indicator bar indicative of a first threshold value of the first parameter associated with the sympathetic nerve function and a second threshold value of the second parameter associated with the parasympathetic nerve function.

5. The physiological information processing apparatus according to claim 1, wherein the physiological information processing apparatus is configured to obtain the physiological information data from an external sensor, and to update the first trend graph and the second trend graph in accordance with a lapse of time.

6. The physiological information processing apparatus according to claim 1, wherein the physiological information processing apparatus is configured to present an alert to a user when at least one of the first parameter and the at least one second parameter shows abnormality.

7. A physiological information processing apparatus comprising:
   a processor;
   a display including a display screen; and
   a memory storing computer-readable instructions,
   wherein, when the computer-readable instructions are executed by the processor, the processor causes the physiological information processing apparatus to:
   obtain a set of physiological information data indicative of physiological information of a subject, the physiological information data including blood pressure data,
   obtain a first parameter associated with a vital sign of the subject based on the physiological information data,
   display a first trend graph showing a temporal change in the first parameter in a first display area of the display screen of the display that displays the physiological information of the subject,
   obtain a second parameter associated with an autonomic nerve function of the subject based on blood pressure data, the second parameter being a parameter associated with a low frequency component of a maximum blood pressure variability,
   display a second trend graph showing a temporal change in the second parameter with a threshold indicator bar indicating a threshold value in a second display area of the display screen of the display that displays the physiological information of the subject, wherein the threshold indicator bar is movable higher or lower according to a user input, and the processor is configured to display a notification when the at least second parameter is lower than the threshold value, and
   display event information associated with the subject and event information associated with the physiological information processing apparatus in a third display area of the display screen,
   wherein the first display area, the second display area and the third display area are displayed next to one another such that the first trend graph over a first time axis of the first display area or the second trend graph over a second time axis of the second display area is synchronized with the event information associated with the physiological information processing apparatus over a third time axis of the third display area,
   wherein the event information associated with the subject includes:
      first event information indicative of an occurrence of arrhythmia with a first bar having a width representing a time period during which the arrhythmia occurs in synchronization with the first graph relating to the vital sign and the second trend graph relating to the autonomic nerve function;
      second event information indicative of an abnormality of the first parameter with a second bar having a width representing a time period during which the abnormality of the first parameter occurs in synchronization with the first and second graphs; and
      third event information associated with a medical treatment on the subject with a third bar having a width representing a time period during which the medical treatment performed to the subject occurs in synchronization with the first and second graphs, and
   wherein the event information associated with the physiological information processing apparatus indicates an abnormality of the physiological information processing apparatus or a failure of attachment between the physiological information processing apparatus and an external sensor configured to obtain the physiological information data, wherein the event information with the physiological information processing apparatus includes a fourth bar having a width representing a time period during which the abnormality of the physiological information processing apparatus or the failure of attachment between the physiological information processing apparatus and the external sensor.

8. A physiological information processing method to be executed by a computer, the physiological information processing method comprising steps of:
   (a) obtaining a set of physiological information data indicative of physiological information of a subject, the physiological information data including blood pressure data;
   (b) obtaining a first parameter associated with a vital sign of the subject based on the physiological information data;
   (c) displaying a first trend graph showing a temporal change in the first parameter in a first display area of a display screen;
   (d) obtaining at least one second parameter associated with an autonomic nerve function of the subject based on the blood pressure data, the at least one second parameter being a parameter associated with a low frequency component of a maximum blood pressure variability;

(e) displaying a second trend graph showing a temporal change in the at least one second parameter with a threshold indicator bar indicating a threshold value in a second display area of the display screen, wherein the threshold indicator bar is movable higher or lower according to a user input, and the processor is configured to display a notification when the at least second parameter is lower than the threshold value; and (f) displaying event information associated with the subject and event information associated with the physiological information processing apparatus in a third display area of the display screen, wherein the first display area, the second display area, and the third display area are displayed next to one another such that the first trend graph over a first time axis of the first display area or the second trend graph over a second time axis of the second display area is synchronized with the event information associated with the physiological information processing apparatus over a third time axis of the third display area, wherein the event information associated with the subject includes:

first event information indicative of an occurrence of arrhythmia with a first bar having a width representing a time period during which the arrhythmia occurs in synchronization with the first graph relating to the vital sign and the second trend graph relating to the autonomic nerve function;

second event information indicative of an abnormality of the first parameter with a second bar having a width representing a time period during which the abnormality of the first parameter occurs in synchronization with the first and second graphs; and third event information associated with a medical treatment on the subject with a third bar having a width representing a time period during which the medical treatment performed to the subject occurs in synchronization with the first and second graphs, and wherein the event information associated with the physiological information processing apparatus indicates an abnormality of the physiological information processing apparatus or a failure of attachment between the physiological information processing apparatus and an external sensor configured to obtain the physiological information data, wherein the event information with the physiological information processing apparatus includes a fourth bar having a width representing a time period during which the abnormality of the physiological information processing apparatus or the failure of attachment between the physiological information processing apparatus and the external sensor.

9. The physiological information processing method according to claim 8, wherein displaying the second trend graph includes displaying the second trend graph and a threshold indicator bar of the at least one second parameter in the second display area.

10. The physiological information processing method according to claim 9, further comprising a step of (g) moving the threshold indicator bar in accordance with an input operation from a user.

11. The physiological information processing method according to claim 9, wherein obtaining the at least one second parameter includes obtaining a plurality of second parameters, the plurality of second parameters comprising:

a first parameter associated with a sympathetic nerve function of the patient; and a second parameter associated with a parasympathetic nerve function of the patient, wherein displaying the second trend graph includes displaying, in the second display area, the second trend graph showing the temporal change in the first parameter associated with the sympathetic nerve function and showing the temporal change in the second parameter associated with the parasympathetic nerve function, and wherein the threshold indicator bar is a single threshold indicator bar indicative of a first threshold value of the first parameter associated with the sympathetic nerve function and a second threshold value of the second parameter associated with the parasympathetic nerve function.

12. The physiological information processing method according to claim 8, wherein obtaining the set of physiological information data includes obtaining the physiological information data from an external sensor, displaying the first trend graph includes updating the first trend graph in accordance with a lapse of time, and displaying the second trend graph includes updating the second trend graph in accordance with the lapse of time.

13. A non-transitory computer-readable storage medium storing a program which causes a computer to execute the physiological information processing method according to claim 8.

* * * * *